(12) United States Patent
Kontani et al.

(10) Patent No.: US 9,535,214 B2
(45) Date of Patent: Jan. 3, 2017

(54) METHOD OF INPUTTING LIGHT INTO OPTICAL WAVEGUIDE

(71) Applicant: NITTO DENKO CORPORATION, Ibaraki-shi, Osaka (JP)

(72) Inventors: Tomohiro Kontani, Ibaraki (JP); Mayu Ozaki, Ibaraki (JP)

(73) Assignee: NITTO DENKO CORPORATION, Ibaraki-shi (JP)

( * ) Notice: Subject to any disclaimer, the term of this patent is extended or adjusted under 35 U.S.C. 154(b) by 0 days.

(21) Appl. No.: 14/815,703

(22) Filed: Jul. 31, 2015

(65) Prior Publication Data

US 2016/0041353 A1 Feb. 11, 2016

(30) Foreign Application Priority Data

Aug. 5, 2014 (JP) .................................. 2014-159282

(51) Int. Cl.
G02B 6/42 (2006.01)
G02B 6/12 (2006.01)
G01N 21/55 (2014.01)
G02B 6/122 (2006.01)
G01N 21/552 (2014.01)

(52) U.S. Cl.
CPC ........... G02B 6/1226 (2013.01); G01N 21/553 (2013.01); G02B 6/4292 (2013.01); G02B 6/4296 (2013.01); G02B 6/4298 (2013.01); G02B 6/4204 (2013.01)

(58) Field of Classification Search
CPC .................................................. G02B 6/1226
See application file for complete search history.

(56) References Cited

U.S. PATENT DOCUMENTS

| 5,991,048 | A | * | 11/1999 | Karlson | G01N 21/553 |
| | | | | | 356/445 |
| 6,432,364 | B1 | * | 8/2002 | Negami | G01N 21/553 |
| | | | | | 385/12 |
| 7,920,268 | B2 | * | 4/2011 | Song | G01N 21/7703 |
| | | | | | 250/336.2 |
| 7,999,941 | B2 | * | 8/2011 | Matsushita | G01J 3/02 |
| | | | | | 356/445 |
| 9,075,009 | B2 | * | 7/2015 | Kim | G01N 21/552 |

(Continued)

FOREIGN PATENT DOCUMENTS

JP 200019100 A 1/2000
JP 2007263736 A 10/2007

(Continued)

*Primary Examiner* — Michelle R Connelly
(74) *Attorney, Agent, or Firm* — Alleman Hall McCoy Russell & Tuttle LLP

(57) ABSTRACT

The present invention provides a method of inputting light into a core layer of a multimode optical waveguide. The optical waveguide includes an under-cladding layer; and the core layer formed so that at least a part of the core layer is adjacent to the under-cladding layer. The method includes inputting the light into the core layer so that a spot of the light at an input port-side end surface of the multimode optical waveguide completely includes an input port of the core layer; a spot area of the light at the input port-side end surface of the multimode optical waveguide is twice or more of an area of the input port of the core layer; and an angle of input range of the light at an input port end surface of the core layer is from 10° to 30°.

5 Claims, 3 Drawing Sheets

(56) References Cited

U.S. PATENT DOCUMENTS

| | | | |
|---|---|---|---|
| 2004/0105644 A1* | 6/2004 | Dawes | G02B 6/122 385/129 |
| 2007/0222998 A1* | 9/2007 | Sasaki | G06K 9/0004 356/445 |
| 2009/0142016 A1* | 6/2009 | Aksyuk | B82Y 20/00 385/14 |
| 2009/0303489 A1* | 12/2009 | Allsop | B82Y 20/00 356/445 |
| 2013/0077912 A1* | 3/2013 | Kontani | G01N 21/553 385/12 |
| 2013/0259418 A1* | 10/2013 | Kontani | G01N 21/553 385/12 |
| 2014/0017125 A1* | 1/2014 | Kontani | G01N 21/03 422/69 |
| 2014/0017126 A1* | 1/2014 | Kontani | G01N 21/03 422/69 |
| 2014/0045730 A1* | 2/2014 | Walters | G01N 21/553 506/39 |
| 2014/0132959 A1* | 5/2014 | Kontani | G01N 21/553 356/445 |
| 2014/0363336 A1* | 12/2014 | Kontani | G01N 21/553 422/69 |
| 2015/0029502 A1* | 1/2015 | Kontani | G01N 21/553 356/246 |
| 2015/0042998 A1* | 2/2015 | Kontani | G01N 21/553 356/445 |
| 2015/0147021 A1* | 5/2015 | Kontani | G01N 21/553 385/12 |
| 2015/0260649 A1* | 9/2015 | Nishio | G01N 21/553 385/12 |

FOREIGN PATENT DOCUMENTS

| | | | | |
|---|---|---|---|---|
| WO | WO 0045154 A1 * | 8/2000 | | B82Y 20/00 |
| WO | WO 2007118714 A1 * | 10/2007 | | B82Y 20/00 |
| WO | 2008075578 A1 | 6/2008 | | |

\* cited by examiner

METHOD OF INPUTTING LIGHT INTO OPTICAL WAVEGUIDE

This application claims priority under 35 U.S.C. Section 119 to Japanese Patent Application No. 2014-159282 filed on Aug. 5, 2014, which is herein incorporated by reference.

BACKGROUND OF THE INVENTION

Field of the Invention

The present invention relates to a method of inputting light into an optical waveguide.

Description of the Related Art

In recent years, as a small high-sensitivity sensor, a sensor has been proposed which includes a planar polymer optical waveguide, and optionally includes a sensing film reacting with a predetermined substance, a metal thin-film, and the like, for performing various chemical analyses and/or biochemical analyses through use of an evanescent wave generated on a surface of the polymer optical waveguide (for example, International Patent WO2008/75578 and Japanese Patent Application Laid-open Nos. 2000-19100 and 2007-263736).

However, there is an increasing demand for detection of a minute change and/or a trace amount of a component with a small sample amount, and thus further enhancement of detection sensitivity is also being demanded in analysis using the above-mentioned sensor. In particular, from a viewpoint of a signal/noise (S/N) ratio, it is important to enhance a signal.

SUMMARY OF THE INVENTION

The present invention has been made in view of solving the related-art problems, and an object of the present invention is to provide a sensor (for example, SPR sensor) having very excellent detection sensitivity (for example, S/N ratio) and the like.

In the above-mentioned sensor, when light is input into a core of an optical waveguide, light having a diameter that is substantially the same as a core diameter is generally input into the core through a collimator, a collective lens, an optical fiber, and the like. In contrast, as a result of investigations, the inventors of the present invention found that light from a light source is significantly lost through the optical fiber and the like, and the amount of light to be guided in the core is increased to obtain a large signal when the light is input into the core under the particular conditions below, thereby achieving the present invention.

The present invention provides a method of inputting light into a core layer of a multimode optical waveguide including an under-cladding layer and the core layer formed so that at least a part of the core layer is adjacent to the under-cladding layer. In the method, a spot of the light at an input port-side end surface of the multimode optical waveguide completely includes an input port of the core layer, and a spot area of the light at the input port-side end surface of the multimode optical waveguide is twice or more of an area of the input port of the core layer. Further, an angle of input range of the light at an input port end surface of the core layer is from 10° to 30°.

In one embodiment, a spot diameter of the light at the input port-side end surface of the multimode optical waveguide is 100 μm or more.

According to another aspect of the present invention, an SPR sensor measurement method is provided. The method includes inputting light into a core layer of an SPR sensor cell through use of the light inputting method. The SPR sensor cell includes (i) a multimode optical waveguide including an under-cladding layer and the core layer formed so that at least a part of the core layer is adjacent to the under-cladding layer and (ii) a metal layer covering the core layer.

According to still another aspect of the present invention, an SPR sensor is provided. The SPR sensor of the present invention includes (i) an SPR sensor cell including (a) a multimode optical waveguide including an under-cladding layer and a core layer formed so that at least a part of the core layer is adjacent to the under-cladding layer and (b) a metal layer covering the core layer, and (ii) a light source. The light source is arranged so that, at an input port-side end surface of the multimode optical waveguide, light output from the light source forms a spot that completely includes an input port of the core layer and has an area that is twice or more of an area of the input port of the core layer, and so that the light is input into an input port end surface of the core layer in an angle of input range from 10° to 30°.

In another embodiment of the present invention, the SPR sensor of the present invention includes (i) an SPR sensor cell including (a) a multimode optical waveguide including an under-cladding layer and a core layer formed so that at least a part of the core layer is adjacent to the under-cladding layer and (b) a metal layer covering the core layer, (ii) a light source, and (iii) means such as an optical component for causing light output from the light source to form, at an input port-side end surface of the multimode optical waveguide, a spot that completely includes an input port of the core layer and has an area that is twice or more of an area of the input port of the core layer, and inputting the light into an input port end surface of the core layer in an angle of input range from 10° to 30°.

According to the one embodiment of the present invention, the light from the light source may be guided in the core efficiently by inputting the light into the core under the particular conditions. As a result, the intensity (that is, signal intensity) of the output light transmitted through the core is increased, and hence measurement with high accuracy may be performed. Further, the effect that an inexpensive light source may be used is also obtained.

DETAILED DESCRIPTION OF THE PREFERRED EMBODIMENTS

The light inputting method of the present invention is a method involving inputting light into a core layer of a multimode optical waveguide including an under-cladding layer and the core layer formed so that at least a part of the core layer is adjacent to the under-cladding layer. In the light inputting method of the present invention, a spot of the light at an input port-side end surface of the optical waveguide completely includes an input port of the core layer, a spot area of the light at the input port-side end surface of the optical waveguide is twice or more of an area of the input port of the core layer, and an angle of input range of the light at an input port end surface of the core layer is from 10° to 30°. When the light output from the light source is input into the core layer under the above-mentioned conditions, the light can be guided in the core layer efficiently while a light amount loss such as a connection loss is reduced compared to a related-art light inputting method. As a result, the intensity (that is, signal intensity) of the output light transmitted through the core layer can be increased, and hence analysis and measurement with high accuracy can be performed.

Figure 1:
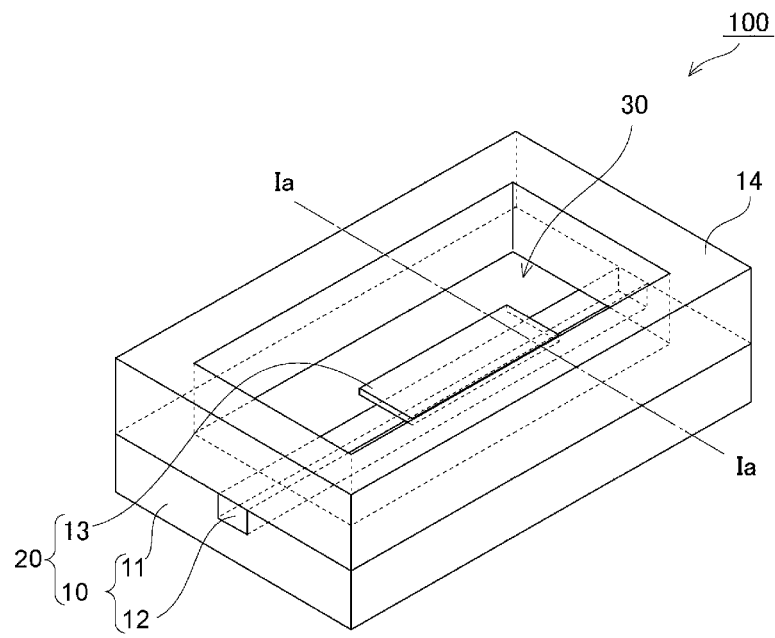
FIG. 1 is a schematic perspective view for illustrating an SPR sensor cell to be used preferably in the present invention.
Figure 2:
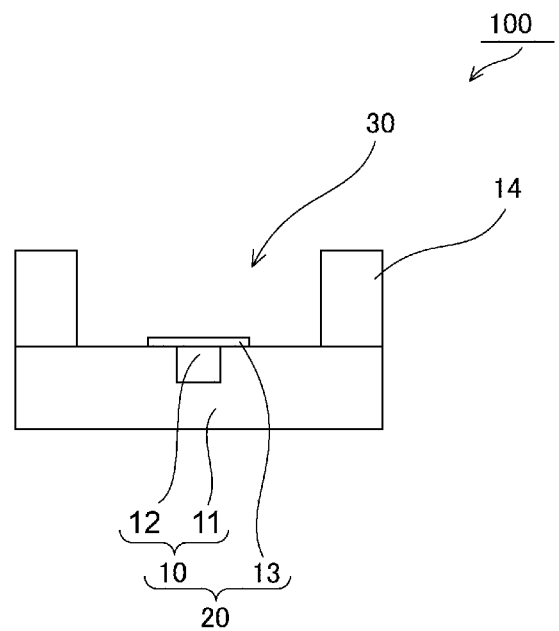
FIG. 2 is a schematic sectional view taken along a line Ia-Ia of the SPR sensor cell of FIG. 1.

It is preferred that the optical waveguide form a detection unit of a sensor for chemical analysis or biochemical analysis from a viewpoint of obtaining the effects of the present invention preferably. FIG. 1 is a schematic perspective view for illustrating an SPR sensor cell in which an optical waveguide forms a part of a detection unit, and FIG. 2 is a schematic sectional view thereof. As illustrated in FIG. 1 and FIG. 2, an SPR sensor cell 100 is formed into a bottomed frame shape having a substantially rectangular shape in a plan view, and includes an optical waveguide 10 including an under-cladding layer 11 and a core layer 12 buried in the under-cladding layer 11 so that an upper surface thereof is exposed, and a metal layer 13 that covers a part of the under-cladding layer 11 and the core layer 12. The optical waveguide 10 and the metal layer 13 serve as a detection unit 20 configured to detect a state and/or a change of a sample. In the illustrated embodiment, the SPR sensor cell 100 includes a sample placing portion 30 provided so as to be adjacent to the detection unit 20. The sample placing portion 30 is defined by an over-cladding layer 14. The over-cladding layer 14 may be omitted as long as the sample placing portion 30 can be provided appropriately. In the sample placing portion 30, a sample (for example, a solution or powder) to be analyzed is placed so as to come into contact with the detection unit (substantially, the metal layer).

The under-cladding layer 11 is formed into a shape of a plate having a substantially rectangular shape in a plan view, with a predetermined thickness. The thickness of the under-cladding layer (thickness from an upper surface of the core layer) is, for example, from 5 μm to 400 μm.

The under-cladding layer 11 may be formed by any suitable material having a lower refractive index than the core layer described later. Specific examples thereof include a fluorine resin, an epoxy resin, a polyimide resin, a polyamide resin, a silicone resin, an acrylic resin, and modified products thereof (for example, a fluorene-modified product, a deuterium-modified product, and a fluorine-modified product in the case of the resins other than the fluorine resin). Those resins may be used alone or in combination. Those resins each can be used as a photosensitive material preferably by being blended with a photosensitizing agent.

The under-cladding layer 11 may contain particles in addition to the above-mentioned resins. The S/N ratio can be further enhanced by dispersing the particles in the under-cladding layer 11. As the particles, any suitable particles capable of increasing the light reflectance of a surface of the under-cladding layer 11 and/or reducing the light transparency in the under-cladding layer 11 can be used. In the case where the particles are dispersed in the under-cladding layer 11, the light reflectance of the under-cladding layer 11 at a wavelength of 650 nm may be, for example, 7% or more, preferably 10% or more.

As a material for forming the above-mentioned particles, for example, there is given a metal or an inorganic oxide. Further, an average particle diameter (φ) of the particles is, for example, from 10 nm to 5 μm, preferably from 200 nm to 2.5 μm. A filling ratio of the particles in the under-cladding layer 11 is, for example, from 1% to 50%, preferably from 2% to 30%.

The core layer 12 is formed into a substantially square column shape extending in a direction orthogonal to both a width direction (right and left direction of the drawing sheet of FIG. 2) and a thickness direction of the under-cladding layer 11, and is buried in an upper end portion of the under-cladding layer 11 substantially at the center thereof in the width direction. The direction in which the core layer 12 extends serves as a direction in which light is propagated in the optical waveguide 10.

The core layer 12 is arranged so that the upper surface thereof is flush with an upper surface of the under-cladding layer 11. The metal layer 13 can be arranged efficiently only on an upper side of the core layer 12 by arranging the core layer 12 so that the upper surface thereof is flush with the upper surface of the under-cladding layer 11. Further, the core layer 12 is arranged so that both end surfaces thereof in the extending direction are flush with both end surfaces of the under-cladding layer 11 in the extending direction.

A refractive index ($N_{CO}$) of the core layer 12 is higher than a refractive index ($N_{CL}$) of the under-cladding layer 11. A difference ($N_{CO}-N_{CL}$) between the refractive index of the core layer 12 and that of the under-cladding layer 11 is preferably 0.010 or more, more preferably 0.020 or more, still more preferably 0.025 or more. When the difference between the refractive index of the core layer 12 and that of the under-cladding layer 11 falls within such range, the optical waveguide 10 of the detection unit 20 can be set to a so-called multimode. Further, the difference between the refractive index of the core layer 12 and that of the under-cladding layer 11 is preferably 0.15 or less, more preferably 0.10 or less, still more preferably 0.050 or less. When the difference between the refractive index of the core layer 12 and that of the under-cladding layer 11 falls within such range, light having an angle of reflection, at which SPR excitation occurs, can exist in the core layer 12.

The refractive index ($N_{CO}$) of the core layer 12 in an SPR sensor cell application is preferably 1.43 or less, more preferably less than 1.40, still more preferably 1.38 or less. The detection sensitivity can be enhanced significantly by setting the refractive index of the core layer 12 to 1.43 or less. The lower limit of the refractive index of the core layer 12 is preferably 1.34. When the refractive index of the core layer 12 is 1.34 or more, SPR can be excited even in a sample of an aqueous solution system (refractive index of water: 1.33), and a general-purpose material can be used.

The thickness of the core layer 12 is, for example, from 5 μm to 200 μm, preferably from 20 μm to 200 μm. Further, the width of the core layer 12 is, for example, from 5 μm to 200 μm, preferably from 20 μm to 200 μm. When the core layer 12 has such thickness and/or width, the optical waveguide 10 can be set to the so-called multimode. Further, the length (waveguide length) of the core layer 12 is, for example, from 2 mm to 50 mm, preferably from 10 mm to 20 mm.

As a material for forming the core layer 12, any suitable material can be used as long as the effects of the present invention can be obtained. For example, the core layer 12 may be formed of a resin that is similar to the resin for forming the under-cladding layer 11 and is adjusted so as to have a higher refractive index than the under-cladding layer 11.

As illustrated in FIG. 1 and FIG. 2, the metal layer 13 is formed so as to uniformly cover at least a part of the upper surfaces of the under-cladding layer 11 and the core layer 12. As necessary, an easy-adhesion layer (not shown) may be formed between the under-cladding layer 11 and the metal layer 13 and between the core layer 12 and the metal layer 13. By forming the easy-adhesion layer, the under-cladding layer 11 and the core layer 12 can be fixed to the metal layer 13 firmly.

As a material for forming the metal layer 13, there may be given gold, silver, platinum, copper, aluminum, and alloys thereof. The metal layer may be a single layer or may have a laminate structure of two or more layers. The thickness (total thickness of all the layers in the case of the laminate structure) of the metal layer is preferably from 20 nm to 70 nm, more preferably from 30 nm to 60 nm.

As a material for forming the easy-adhesion layer, chromium or titanium may typically be given. The thickness of the easy-adhesion layer is preferably from 1 nm to 5 nm.

As illustrated in FIG. 1, the over-cladding layer 14 is formed into the shape of a frame having a rectangular shape in a plan view so that an outer periphery of the over-cladding layer 14 becomes substantially flush with an outer periphery of the under-cladding layer 11 in a plan view, on the upper surface of each of the under-cladding layer 11 and the core layer 12. A portion surrounded by the upper surfaces of the under-cladding layer 11 and the core layer 12 and the over-cladding layer 14 is partitioned as the sample placing portion 30. By placing a sample in the partitioned portion, the metal layer of the detection unit 20 and the sample come into contact with each other so that detection can be performed. Further, by forming such a partitioned portion, a sample can be easily placed on the surface of the metal layer, and hence the operability can be enhanced.

As a material for forming the over-cladding layer 14, for example, there may be given the materials for forming the core layer 12 and the under-cladding layer 11, and silicone rubber. The thickness of the over-cladding layer 14 is preferably from 5 µm to 2,000 µm, more preferably from 25 µm to 200 µm. The refractive index of the over-cladding layer 14 is preferably lower than the refractive index of the core layer 12. In one embodiment, the refractive index of the over-cladding layer 14 is equal to the refractive index of the under-cladding layer 11.

The SPR sensor cell 100 can be manufactured by a manufacturing method disclosed in, for example, Japanese Patent Application Laid-open Nos. 2011-179978 and 2012-215540.

In FIG. 1 and FIG. 2, the SPR sensor cell including the metal layer formed on the optical waveguide is illustrated, but the optical waveguide to be used preferably in the present invention is not limited to this embodiment. Specifically, the effects of the present invention can be obtained through the use of any form of the optical waveguide, as long as the optical waveguide constitutes the detection unit of the sensor, which is configured to perform analysis based on a change in output light from the core layer. For example, a sensing layer having light absorbing characteristics that change due to contact with a sample may be formed on the optical waveguide instead of the metal layer, or a dielectric layer having an antibody or an antigen fixed thereto may be formed on the optical waveguide instead of the metal layer.

As described above, in the present invention, the light from the light source is input into the core layer so that the spot of the light at the input port-side end surface of the optical waveguide completely includes the input port of the core layer, the spot area of the light at the input port-side end surface of the optical waveguide is twice or more of the area of the input port of the core layer, and the angle of input range of the light at the input port end surface of the core layer is from 10° to 30°.

Figure 3:
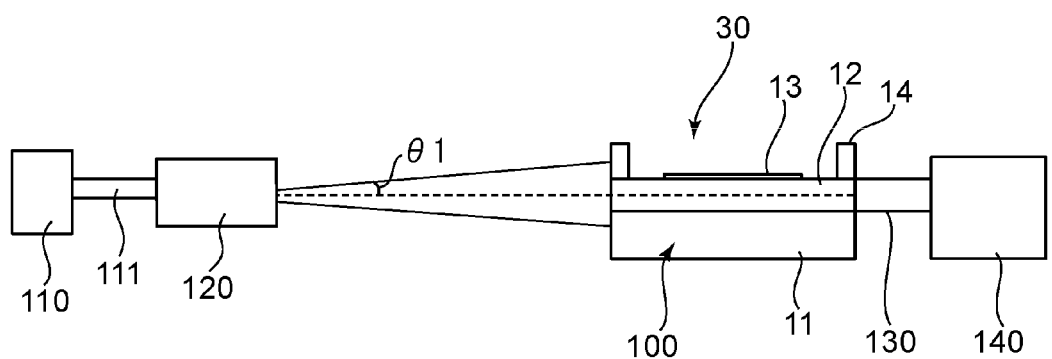
FIG. 3 is a schematic view for illustrating a light inputting method according to a first embodiment of the present invention.
Figure 4:
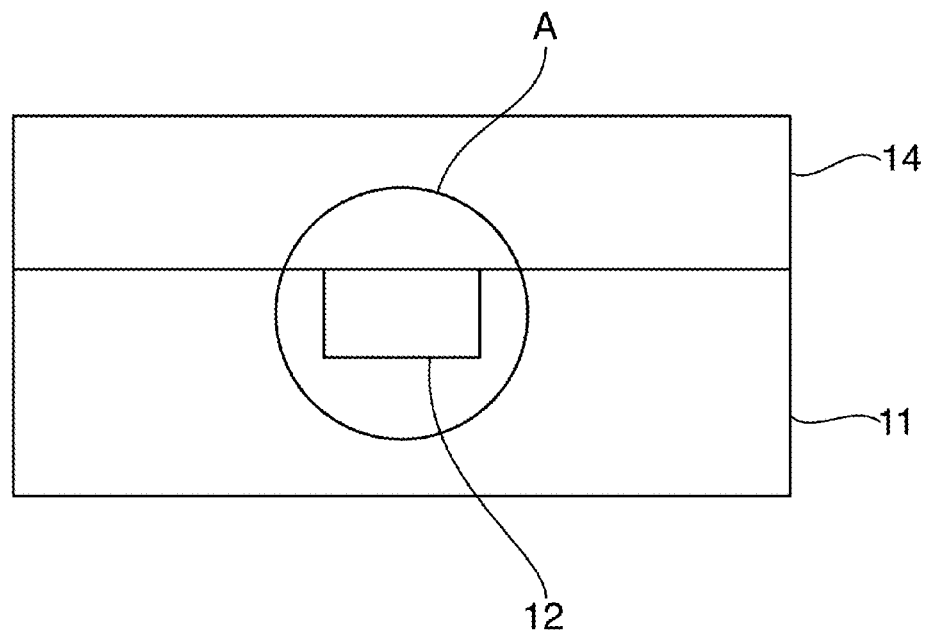
FIG. 4 is a schematic view of the SPR sensor cell when viewed from an input port side in the light inputting method according to the first embodiment of the present invention.

FIG. 3 is a schematic view for illustrating a light inputting method according to a first embodiment of the present invention, which is used to input light into the core layer of the SPR sensor cell illustrated in FIG. 1 and FIG. 2. FIG. 4 is a schematic view of the SPR sensor cell when viewed from an input port side in the first embodiment. Now, the present invention is described in more detail with reference to the drawings.

As illustrated in FIG. 3, a light source 110 and a device 120 are arranged on the input port side of the core layer 12. The device 120 is connected to the light source 110 through an optical connector 111 and is configured to adjust the spot diameter and/or the angle of input range of light. On the other hand, an output port side of the core layer 12 is connected to a light measuring instrument 140 through an optical fiber 130 having the approximately same diameter as that of the output port.

As the light source 110, any suitable light source can be adopted. Specific examples of the light source 110 include a white light source and a monochromatic light source. The optical measuring instrument 140 includes a light-receiving element and is connected to any suitable arithmetic processing device so as to enable accumulation, display, and processing of data.

As the device 120 configured to adjust the spot diameter and/or the angle of input range of light, a limited space excitation optical system device (for example, "M-Scope type G" (trade name) manufactured by Synergy Optosystems Co., Ltd.), a beam expander, a concave lens, or the like can be used.

The angle of input range ($\theta 1$) of light at the input port end surface of the core layer 12 is from 10° to 30°, preferably from 20° to 30°. In such an angle of input range, the incident light can be guided as preferred in the core layer 12. In the illustrated example, diverging light is input into the core layer 12, but converging light may be input into the core layer 12. Note that the angle of input of light at the input port end surface of the core layer 12 refers to an angle formed by an optical axis direction of the incident light and an extending direction of the core layer 12. The angle of input range corresponds to a spread angle of light to be input into the core layer 12 and refers to an angle (half-value angle) at which the intensity of the incident light becomes 50% of that on the optical axis. For example, light having an angle of input range of 10° ($\theta 1=10°$) refers to light having a half-value angle of 10.

Further, as illustrated in FIG. 4, a spot A of light at the input port-side end surface of the SPR sensor cell 100 completely includes the input port of the core layer 12. The area of the spot A is twice or more, preferably four times or more, more preferably six times or more of an area of the input port of the core layer 12. There is no particular limitation on the upper limit of the area of the spot A, and it is preferred that the area of the spot A be set so as to allow light to be input into the core layer 12 in the above-mentioned angle of input range.

The diameter of the spot A is, for example, 80 µm or more, preferably 100 µm or more, more preferably 150 µm or more. When the spot diameter falls within such range, light is allowed to be input into the entire surface of the input port of the core layer 12 in a multimode. There is no particular limitation on the upper limit of the spot diameter, and it is preferred that the spot diameter be set so as to allow light to be input into the core layer 12 in the above-mentioned angle of input range (spread angle).

From a viewpoint of introducing light into the core layer 12 effectively, it is preferred that the optical axis of the incident light (center of the spot A) be substantially aligned with the center of the input port of the core layer 12.

Figure 5:
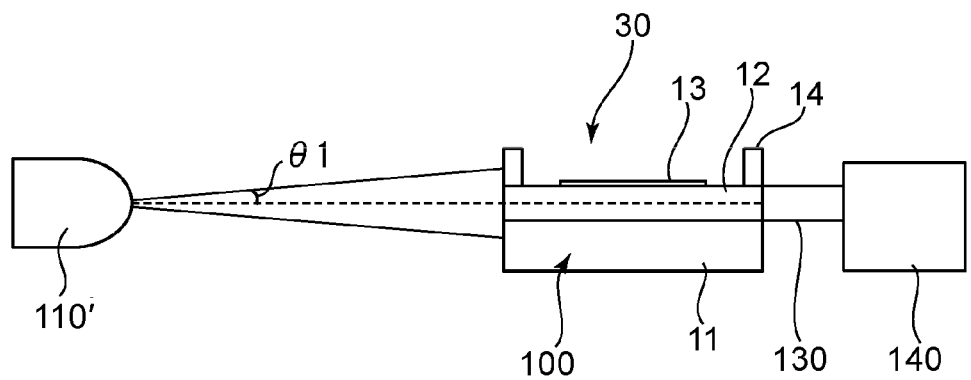
FIG. 5 is a schematic view for illustrating a light inputting method according to a second embodiment of the present invention.

FIG. 5 is a schematic view for illustrating a light inputting method according to a second embodiment of the present invention, which is used to input light into the core layer of the SPR sensor cell illustrated in FIG. 1 and FIG. 2. The second embodiment is different from the first embodiment in that light output from a light source 110' is directly input into the core layer 12. According to this embodiment, light output from the light source 110' can be directly introduced into the core layer 12, and hence there are advantages in that no connection loss is caused, and the operation such as optical connection is simplified. From a viewpoint of obtaining the above-mentioned spread angle, it is preferred that a light source having high directivity (for example, an LED light source, a laser light source) be used.

According to another aspect of the present invention, there is provided an SPR sensor. The SPR sensor of the present invention is preferred for performing the above-mentioned light inputting method.

As illustrated in FIG. 5, an SPR sensor 200b according to one embodiment of the present invention includes (1) the light source 110' and (2) the SPR sensor cell 100 including the multimode optical waveguide 10 that includes the under-cladding layer 11 and the core layer 12 formed so that at least a part of the core layer 12 is adjacent to the under-cladding layer 11, and the metal layer 13 covering the core layer 12. In the SPR sensor 200b, the light source 110' is arranged so that light output from the light source 110' forms, at the input port-side end surface of the optical waveguide 10, a spot that completely includes the input port of the core layer 12 and has an area that is twice or more of an area of the input port of the core layer 12, and so that the light is input into the input port end surface of the core layer 12 in an angle of input range (spread angle) from 10° to 30°.

As illustrated in FIG. 3, an SPR sensor according to another embodiment of the present invention includes (1) the light source 110, (2) the SPR sensor cell 100 including the multimode optical waveguide 10 that includes the under-cladding layer 11 and the core layer 12 formed so that at least a part of the core layer 12 is adjacent to the under-cladding layer 11, and the metal layer 13 covering the core layer 12, and (3) the optical component 120 for causing light output from the light source 110 to form, at the input port-side end surface of the optical waveguide 10, a spot that completely includes the input port of the core layer 12 and has an area that is twice or more of an area of the input port of the core layer 12, and inputting the light into the input port end surface of the core layer 12 in an angle of input range (spread angle) from 10° to 30°. In the SPR sensor 200a illustrated in FIG. 3, the optical component 120 can be, for example, a limited space excitation optical system device, a beam expander, a concave lens, or the like.

Now, an example of a measurement method using the SPR sensor of the present invention is described.

First, a sample is placed on the sample placing portion 30 of the SPR sensor cell 100 so that the sample and the metal layer 13 are brought into contact with each other. Then, light output from the light source 110 is guided to the core layer 12 in a predetermined angle of input range (spread angle) with a predetermined spot diameter. The light guided to the core layer 12 is transmitted through the core layer 12 while repeating total reflection in the core layer 12, and a part of the light is input into the metal layer 13 on an upper surface of the core layer 12 and is attenuated by surface plasmon resonance. The light transmitted through the core layer 12 is guided to the optical measuring instrument 140 through an optical fiber 130. That is, in the SPR sensor, the intensity of light having a wavelength generating surface plasmon resonance in the core layer 12 is attenuated in the light guided to the optical measuring instrument 140. The wavelength of light generating surface plasmon resonance depends on, for example, the refractive index of the sample brought into contact with the metal layer 13. Therefore, by detecting the attenuation of the light intensity of the light guided to the optical measuring instrument 140, a change in the refractive index of the sample can be detected.

For example, in the case of using a white light source as the light source 110, a change in refractive index of the sample can be confirmed by measuring the wavelength of light whose light intensity is attenuated after the transmission through the core layer 12 (wavelength of light generating surface plasmon resonance) with the optical measuring instrument 140 and detecting a change in wavelength of the light whose light intensity is attenuated. In addition, for example, in the case of using a monochromatic light source as the light source 110, a change in wavelength of light generating surface plasmon resonance can be confirmed and a change in refractive index of the sample can be confirmed by measuring a change (attenuation degree) in light intensity of monochromatic light after the transmission through the core layer 12 with the optical measuring instrument 140 and detecting a change in attenuation degree.

EXAMPLES

The present invention is hereinafter described specifically by way of Examples. However, the present invention is not limited to the Examples.

Example 1

An SPR sensor cell as illustrated in FIG. 1 and FIG. 2 was obtained in accordance with a manufacturing method disclosed in Japanese Patent Application Laid-open No. 2012-215540. Specifically, a fluorine-based UV curable resin ("Fluorolink MD700" (trade name) manufactured by Solvay Specialty Polymers Japan K.K.), which was a material for forming an under-cladding layer, was applied to a die having a protrusion corresponding to a core layer formation portion of an under-cladding layer, and the resin was cured with ultraviolet rays to form an under-cladding layer. The refractive index of the under-cladding layer thus obtained was 1.347. The under-cladding layer had a length of 80 mm, a width of 80 mm, and a thickness of 100 μm, and a groove portion for forming a core layer having a width of 50 μm and a thickness (depth) of 50 μm was formed in the under-cladding layer. After the under-cladding layer was peeled from the die, the groove portion was filled with a material for forming a core layer, and was cured with ultraviolet rays to form a core layer. The material for forming a core layer was prepared by dissolving through stirring 60 parts by weight of a fluorine-based UV curable resin ("OP38Z" (trade name) manufactured by DIC Corporation) and 40 parts by weight of a fluorine-based UV curable resin ("OP40Z" (trade name)

manufactured by DIC Corporation). The refractive index of the core layer thus formed was 1.384. Note that the refractive index was measured by forming a thin-film having a thickness of 10 μm on a silicon wafer and measuring the refractive index of the film at a wavelength of 830 nm through use of a prism coupler refractive index measurement device. As described above, a buried-type optical waveguide film was produced.

Then, gold was sputtered onto an upper surface (core layer exposed surface) of the optical waveguide film thus obtained through a mask with an opening having a length of 6 mm and a width of 1 mm, and thus a metal layer (thickness: 30 nm) was formed so as to cover a part of the under-cladding layer and the core layer. Finally, a frame-shaped over-cladding layer was formed by a method similar to that of forming the under-cladding layer through use of the same material as the material for forming an under-cladding layer. Thus, an SPR sensor cell as illustrated in FIG. 1 and FIG. 2 was produced.

A halogen light source ("HL-2000-HP" (trade name) manufactured by Ocean Optics, Inc.), and a limited space excitation optical system device ("M-Scope type G" (trade name) manufactured by Synergy Optosystems Co., Ltd.) were arranged on an input port side of the SPR sensor cell thus obtained and connected to each other as illustrated in FIG. 3. Further, an output port of the core layer was connected to a power meter through an optical fiber having substantially the same diameter (50 μmφ) as that of the output port to obtain an SPR sensor.

In the SPR sensor thus obtained, white light output from a light source was controlled to be input into the core layer in an angle of input range (spread angle) of 14° with a spot diameter of 80 μmφ, and the intensity of light output from the output port of the core layer was measured with the power meter. The results are shown in Table 1.

Examples 2 to 9 and Comparative Examples 1 to 3

The intensity of light output from the output port of the core layer was measured with the power meter in the same way as in Example 1, except that the angle of input range (spread angle) and the spot diameter were controlled to be the values shown in Table 1. The results are shown in Table 1.

Example 10

The intensity of light output from the output port of the core layer was measured with the power meter in the same way as in Example 1, except that an LED light source ("M660F1" (trade name) manufactured by Thorlabs Japan Inc.) was used as a light source, and the spot diameter and the angle of input range (spread angle) were controlled to be the values shown in Table 2. The results are shown in Table 2.

Example 11

An LED light source ("M660F1" (trade name) manufactured by Thorlabs Japan Inc.) was arranged on the input port side of the SPR sensor cell obtained in the same way as in Example 1, as illustrated in FIG. 5. Further, the output port of the core layer was connected to the power meter through an optical fiber having substantially the same diameter (50 μmφ) as that of the output port to obtain an SPR sensor. In the SPR sensor thus obtained, LED light output from the light source was directly input into the core layer, and the intensity of light output from the output port of the core layer was measured with the power meter. The angle of input range of LED light was within the range of 10° to 30°. The results are shown in Table 2.

Comparative Example 4

The input port of the core layer of the SPR sensor cell obtained in the same way as in Example 1 was connected to an LED light source ("M660F1" (trade name) manufactured by Thorlabs Japan, Inc.) through an optical fiber having a diameter of 50 μmφ. Further, the output port of the core layer was connected to the power meter through an optical fiber having substantially the same diameter (50 μmφ) as that of the output port to obtain an SPR sensor. LED light output from the light source was input into the core layer through an optical fiber having a diameter of 50 μmφ in an angle of input range (spread angle) of 8°, and the intensity of light output from the output port of the core layer was measured with the power meter. The results are shown in Table 2.

TABLE 1

|  | Light source | Spot diameter | Spot area ratio (Incident light spot/core layer) | Angle of input range (degree) | Intensity of light (nW) |
|---|---|---|---|---|---|
| Example 1 | White light | 80 μmφ | 2.0 | 14 | 56.1 |
| Example 2 | White light | 160 μmφ | 8.0 | 14 | 60.7 |
| Example 3 | White light | 800 μmφ | 64.0 | 14 | 60.8 |
| Example 4 | White light | 80 μmφ | 2.0 | 20 | 59.3 |
| Example 5 | White light | 160 μmφ | 8.0 | 20 | 64.6 |
| Example 6 | White light | 800 μmφ | 64.0 | 20 | 64.7 |
| Example 7 | White light | 80 μmφ | 2.0 | 26 | 59.7 |
| Example 8 | White light | 160 μmφ | 8.0 | 26 | 65.3 |
| Example 9 | White light | 800 μmφ | 64.0 | 26 | 65.4 |
| Comparative Example 1 | White light | 40 μmφ | 0.5 | 8 | 21.9 |
| Comparative Example 2 | White light | 160 μmφ | 8.0 | 8 | 48.3 |
| Comparative Example 3 | White light | 40 μmφ | 0.5 | 14 | 26.8 |

TABLE 2

|  | Light source | Spot diameter | Spot area ratio (Incident light spot/core layer) | Angle of input range (degree) | Intensity of light (nW) |
|---|---|---|---|---|---|
| Example 10 | LED | 800 μmφ | 64.0 | 20 | 34.8 |
| Example 11 | LED | Direct | 1,256.0 | — | 496.6 |
| Comparative Example 4 | LED | 50 μmφ | 0.785 | 8 | 10.9 |

Example 12

The input port of the core layer of the SPR sensor cell obtained in the same way as in Example 1 was connected to a halogen light source ("HL-2000-HP" (trade name) manufactured by Ocean Optics, Inc.) through an optical fiber having a diameter of 1,000 μmφ. Further, the output port of the core layer was connected to the power meter through an optical fiber having substantially the same diameter (50 μmφ) as that of the output port to obtain an SPR sensor. In the SPR sensor thus obtained, white light output from the light source was input into the core layer through an optical fiber having a diameter of 1,000 μmφ in an angle of input range (spread angle) of 19° and the intensity of light output from the output port of the core layer was measured with the power meter. The results are shown in Table 3.

Comparative Example 5

The intensity of light output from the output port of the core layer was measured with the power meter in the same way as in Comparative Example 4, except that a halogen light source ("HL-2000-HP" (trade name) manufactured by Ocean Optics, Inc.) was used as a light source. The results are shown in Table 3.

TABLE 3

|  | Light source | Spot diameter | Spot area ratio (Incident light spot/core layer) | Angle of input range (degree) | Intensity of light (nW) |
|---|---|---|---|---|---|
| Example 12 | White light | 1,000 μmφ | 314.0 | 19 | 850.4 |
| Comparative Example 5 | White light | 50 μmφ | 0.785 | 8 | 309.7 |

Reference Example 1

Output Under Condition without Optical Waveguide

A halogen light source ("HL-2000-HP" (trade name) manufactured by Ocean Optics, Inc.) was connected to a power meter through an optical fiber having a diameter of 1,000 μmφ and then through an optical fiber having a diameter of 50 μmφ. In this state, white light was output from the light source, and the intensity of light output from the optical fiber having a diameter of 50 μmφ was measured with the power meter. The intensity of the light thus measured was 1,246 μW.

Reference Example 2

Output Under a Condition without an Optical Waveguide

An LED light source ("M660F1" (trade name) manufactured by Thorlabs Japan, Inc.) was connected to a power meter through an optical fiber having a diameter of 1,000 μmφ and then through an optical fiber having a diameter of 50 μmφ. In this state, LED light was output from the light source, and the intensity of light output from the optical fiber having a diameter of 50 μmφ was measured with the power meter. The intensity of the light thus measured was 1,132 μW.

<Evaluation>

As shown in Tables 1 to 3, in the examples in which light was input into the core layer under the particular conditions, the intensity of the output light increased compared to that obtained from the comparative examples. Thus, in the case of performing measurement by the sensor including the optical waveguide in the detection unit through use of such a light inputting method, a larger signal can be obtained.

The light inputting method of the present invention can be preferably used for measurement by a sensor using an optical waveguide such as an SPR sensor.

Many other modifications will be apparent to and be readily practiced by those skilled in the art without departing from the scope and spirit of the invention. It should therefore be understood that the scope of the appended claims is not intended to be limited by the details of the description but should rather be broadly construed.

The invention claimed is:

1. A method of inputting light into a core layer of a multimode optical waveguide,
   the optical waveguide including:
   an under-cladding layer; and
   the core layer formed so that at least a part of the core layer is adjacent to the under-cladding layer,
   the method comprising inputting the light into the core layer so that:
   a spot of the light at an input port-side end surface of the multimode optical waveguide completely includes an input port of the core layer;
   a spot area of the light at the input port-side end surface of the multimode optical waveguide is twice or more of an area of the input port of the core layer; and
   an angle of input range of the light at an input port end surface of the core layer is from 10° to 30°.

2. The method according to claim 1, wherein a spot diameter of the light at the input port-side end surface of the multimode optical waveguide is 100 μm or more.

3. An SPR sensor measurement method, comprising inputting light into the core layer of an SPR sensor cell through use of the method of claim 1, the SPR sensor cell including:
  the multimode optical waveguide including:
    the under-cladding layer; and
    the core layer formed so that at least a part of the core layer is adjacent to the under-cladding layer; and
  a metal layer covering the core layer.

4. An SPR sensor, comprising:
an SPR sensor cell including:
  a multimode optical waveguide including:
    an under-cladding layer; and
    a core layer formed so that at least a part of the core layer is adjacent to the under-cladding layer; and
  a metal layer covering the core layer; and
a light source,
the light source being arranged so that, at an input port-side end surface of the multimode optical waveguide, light output from the light source forms a spot that completely includes an input port of the core layer and has an area that is twice or more of an area of the input port of the core layer, and so that the light is input into an input port end surface of the core layer in an angle of input range from 10° to 30°.

5. An SPR sensor, comprising:
an SPR sensor cell including:
  a multimode optical waveguide including:
    an under-cladding layer; and
    a core layer formed so that at least a part of the core layer is adjacent to the under-cladding layer; and
  a metal layer covering the core layer;
a light source; and
an optical component for causing light output from the light source to form, at an input port-side end surface of the multimode optical waveguide, a spot that completely includes an input port of the core layer and has an area that is twice or more of an area of the input port of the core layer, and inputting the light into an input port end surface of the core layer in an angle of input range from 10° to 30°.

* * * * *